United States Patent [19]

Espina

[11] Patent Number: 5,935,115

[45] Date of Patent: Aug. 10, 1999

[54] SUPRAPUBIC CATHETER LEAK COLLECTION DEVICE

[75] Inventor: Eden R. Espina, Burnham, Ill.

[73] Assignee: Saint Margaret Mercy Healthcare Centers, Inc., Hammond, Ind.

[21] Appl. No.: 09/039,087

[22] Filed: Mar. 13, 1998

Related U.S. Application Data

[60] Provisional application No. 60/042,545, Mar. 27, 1997.

[51] Int. Cl.$^6$ .......................... A61M 31/00; A61F 5/445
[52] U.S. Cl. .......................... 604/277; 604/276; 604/332
[58] Field of Search ...................................... 604/275, 276, 604/277, 278, 332, 355, 338, 339

[56] References Cited

U.S. PATENT DOCUMENTS

| | | | |
|---|---|---|---|
| 3,581,732 | 6/1971 | Ruiz | 604/278 |
| 4,050,461 | 9/1977 | Ruby | 604/277 |
| 4,721,508 | 1/1988 | Burton | 604/277 |
| 5,236,426 | 8/1993 | Schottes et al. | 604/277 |
| 5,738,661 | 4/1998 | Larice | 604/332 |

*Primary Examiner*—Robert A. Clarke
*Attorney, Agent, or Firm*—McAndrews, Held & Malloy, Ltd.

[57] ABSTRACT

A suprapubic fluid collection device contains leakage from an ostomy site. The device comprises an adhesive patch, a collection bag, and a urinary catheter. The adhesive patch has adhesive on one side for securing the patch around the ostomy site and a ring member projecting from the other side. The ring member circumscribes the ostomy site. The collection bag has a first opening and a channel member circumscribing the first opening and projecting from the exterior of the collection bag. The channel member of the collection bag mates with and secures the ring member of the adhesive patch. The collection bag has a second opening formed therein and a drainage spout communicating with the interior of the collection bag. The urinary catheter extends within the interior of the collection bag between the second opening and the first opening. The catheter has a distal end for insertion within a human bladder and a proximal end. The catheter has a first inflatable balloon for securing the distal end within the bladder, a second inflatable balloon for securing and fluidly sealing the catheter within the second opening, and a lumen for conducting fluid from the distal end to the proximal end for subsequent removal from the catheter.

10 Claims, 2 Drawing Sheets

SUPRAPUBIC CATHETER LEAK COLLECTION DEVICE

This application claim benefit of Provisionnal Application Ser. No. 60/042,545 filed Mar. 27, 1997.

FIELD OF THE INVENTION

The present invention relates to urinary catheters and more particularly to a leak collection device for a suprapubic urinary catheter inserted at an ostomy site.

BACKGROUND OF THE INVENTION

Patients with surgically formed ostomy sites for accessing the bladder must use a suprapubic catheter to discharge urine. A suprapubic catheter has a hollow urinary discharge tube that is inserted into the ostomy site and extended into the bladder. An integral balloon located a short distance from the distal end of the catheter is inflated to secure the catheter tube in place within the bladder. The balloon is inflatable from a port located at the proximal end of the catheter, near the opening of the discharge tube.

Patients who use suprapubic catheters over an extended period of time tend to develop leakage around the ostomy site. Such leakage is caused primarily by muscle atrophy and constant movement of the catheter about the ostomy site. The conventional approach to overcoming leakage problems is to increase the diameter of the catheter to form a better seal with the ostomy site stoma and also to increase the size of the balloon to better secure the catheter tip within the bladder. However, the muscle around the ostomy site will continue to atrophy and the catheter. will continue to move about the ostomy site, thereby inducing leakage even when using a larger diameter catheter.

The present leak collection device contains urine leaks from around the ostomy site by providing a collection bag that adheres to the patient's skin and surrounds the ostomy site. The device avoids the progressive enlargement of the size of the ostomy site and prevents degeneration of the skin around the ostomy site.

SUMMARY OF THE INVENTION

A suprapubic fluid collection device contains leakage from an ostomy site. The device comprises an adhesive patch, a collection bag, and a urinary catheter.

The adhesive patch has adhesive on one side for securing the patch around the ostomy site. The adhesive patch also has a ring member projecting from the other side. The ring member circumscribes the ostomy site.

The collection bag has a first opening communicating with the interior thereof. The collection bag further includes a channel member circumscribing the first opening and projecting from the exterior of the collection bag. The channel member mates with and secures the ring member. The collection bag has a second opening formed therein and a drainage spout communicating with the interior of the collection bag.

The urinary catheter extends within the interior of the collection bag between the second opening and the first opening. The catheter has a distal end for insertion within a human bladder and a proximal end. The catheter has a first lumen formed therein for inflating a first balloon to secure the distal end within the bladder. The catheter has a second lumen formed therein for inflating a second balloon for securing and fluidly sealing the catheter within the second opening. The catheter has a third lumen for conducting fluid from the distal end to the proximal end for subsequent removal from the catheter.

In the preferred device, the drainage spout has a shut-off clamp.

DETAILED DESCRIPTION OF THE PREFERRED EMBODIMENTS

Figure 1:
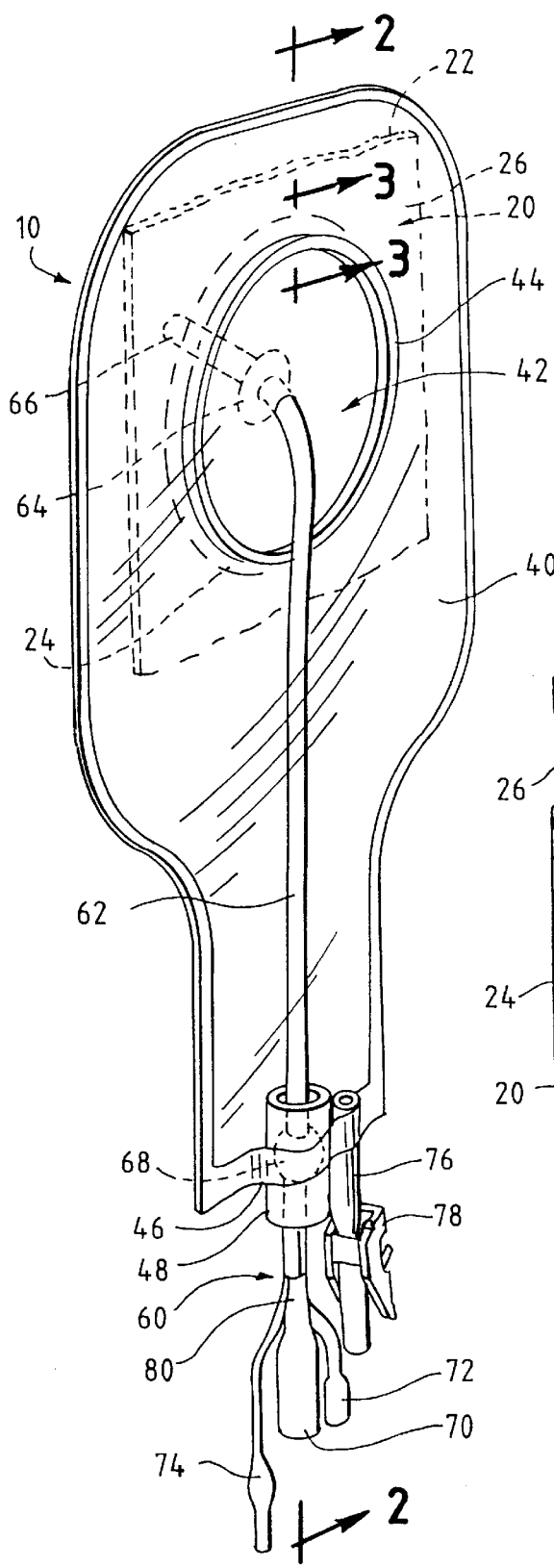
FIG. 1 is a perspective view of the suprapubic leak collection device showing the urinary catheter, leak collection bag, and adhesive patch.

Turning first to FIG. 1, a suprapubic catheter leak collection device 10 includes an adhesive patch 20, a collection bag 40, and a urinary catheter 60. Adhesive patch 20 has an adhesive member 26 with adhesive 22 disposed on one side for adhering the patch 20 to the patient's skin. A ring member 24 projects from the other side of patch 20. Ring member 24 circumscribes the patient's ostomy site.

As further shown in FIG. 1, collection bag 40 has a first opening 42 formed therein. A channel member 44 circumscribes opening 42 and projects from the exterior of collection bag 40. Channel member 44 mates with and secures ring member 24, thereby attaching collection bag 40 to adhesive patch 20. Collection bag 40 has a second opening 46 formed therein. A catheter spout 48 extends into second opening 46 and facilitates the threading of the urinary catheter into collection bag 40. A drainage spout 76 communicates with the interior of collection bag 40. Drainage spout 76 has a shut-off clamp 78.

FIG. 1 also shows a urinary catheter 60 with a distal end 66 for insertion into the patient's bladder (not shown) and a proximal end 80. Catheter 60 extends within the interior of collection bag 40 between second opening 46 and first opening 42. Catheter 60 has a first lumen formed therein for inflating a first balloon 64 to secure distal end 66 within the bladder. First balloon port 72 communicates with the first lumen to allow inflation of first balloon 64. Catheter 60 also has a second lumen formed therein for inflating a second balloon 68 for securing and fluidly sealing catheter 60 within the second opening 46 of collection bag 40. A second balloon port 74 communicates with the second lumen to allow inflation of the second balloon 68. A third lumen conducts fluid from the distal end 66 to the proximal end 80 of catheter 60. A drainage port 70 communicating with the third lumen permits the attachment of additional tubing to remove fluid from catheter 60.

Figure 2:
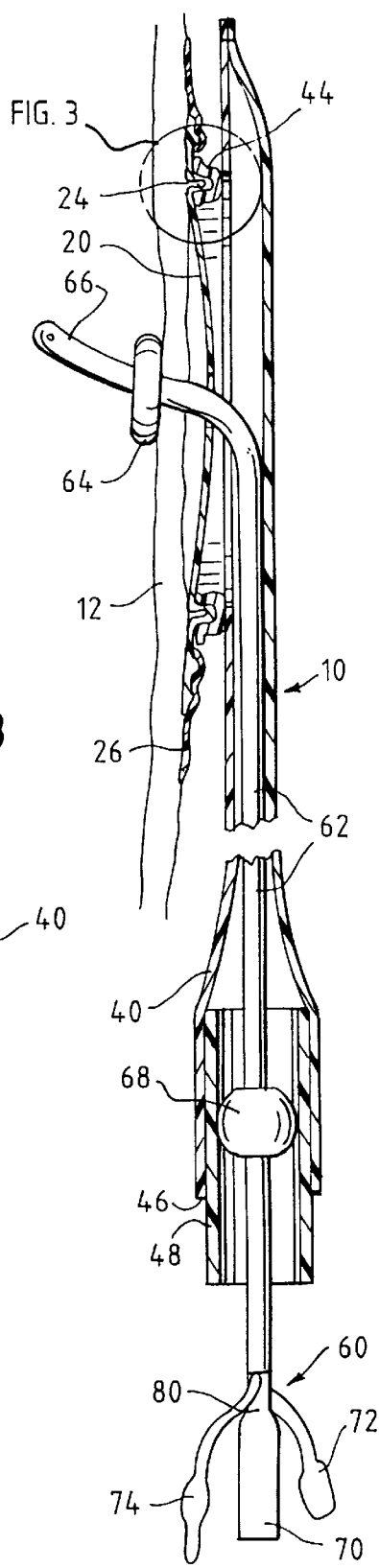
FIG. 2 is a sectional view of the suprapubic leak collection device, taken in the direction of arrows 2—2 in FIG. 1.

FIG. 2 shows a cross-section of the leak collection device 10. Adhesive member 26 secures adhesive patch 20 to the patient's ostomy site 12. The ring member 24 of adhesive patch 20 projects from the ostomy site 12 to attach the collection bag 40 using a press-fit connection with cooperating channel member 44.

FIG. 2 also shows the catheter spout 48 extending from opening 46 in collection bag 40. Prior to inflation of the balloons 64, 68, catheter tube 62 is fed through the catheter spout 48 and the openings in collection bag 40 and adhesive patch 20. Catheter tube 62 is then inserted into the opening in the patient's ostomy site 12 until the distal end 66 is located within the patient's bladder (not shown). Once the distal end 66 of catheter 60 is in place, sterilized water is introduced into balloon port 72 to inflate balloon 64 to retain the distal end 66 in its proper position within the bladder. Pressurized air is introduced into balloon port 74 to create a seal between catheter tube 62 and the catheter spout 48, thereby preventing leakage from collection bag 40. Drainage port 70 at the proximal end 80 directs fluid from catheter 60.

Figure 3:
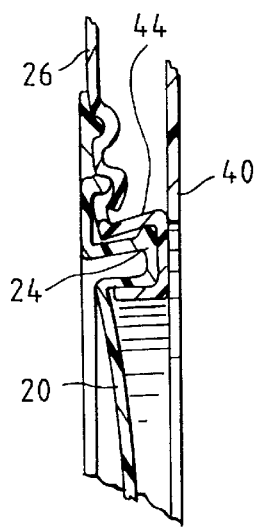
FIG. 3 is an enlarged sectional view of the assembled press-fit connection between the adhesive patch and leak collection bag, the location of which is circled in FIG. 2.
Figure 4:
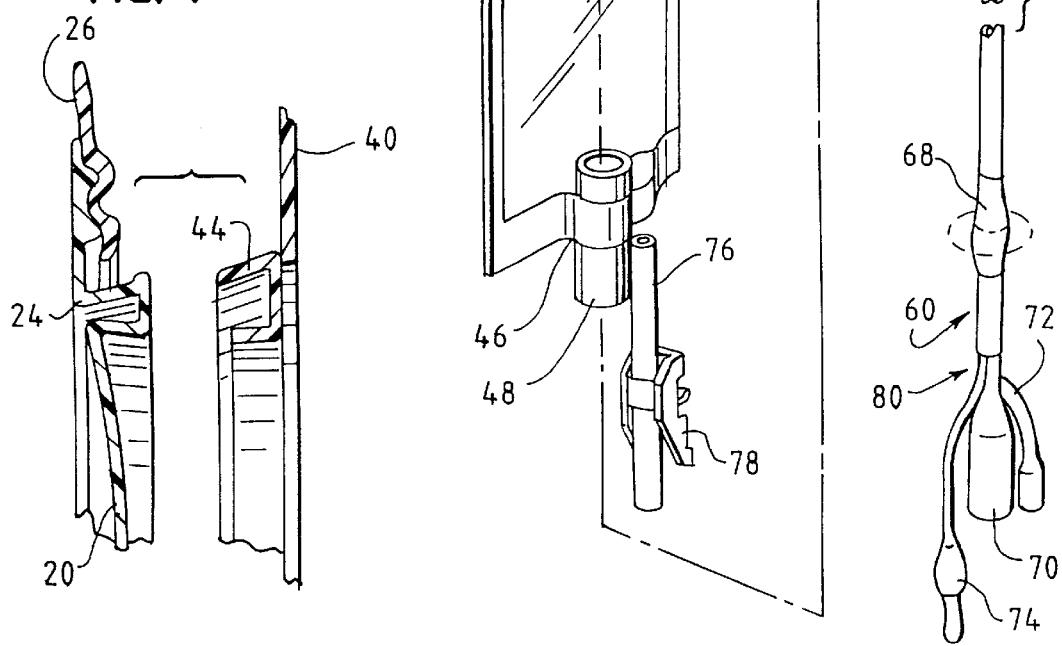
FIG. 4 is a sectional view of the disassembled press-fit connection between the adhesive patch and leak collection bag.

FIGS. 3 and 4 show the connection between ring member 24 of adhesive patch 20 and channel member 44 of collection bag 40. Ring member 24 forms a press-fit connection within channel member 44 to attach collection bag 40 to adhesive patch 20.

Figure 5:
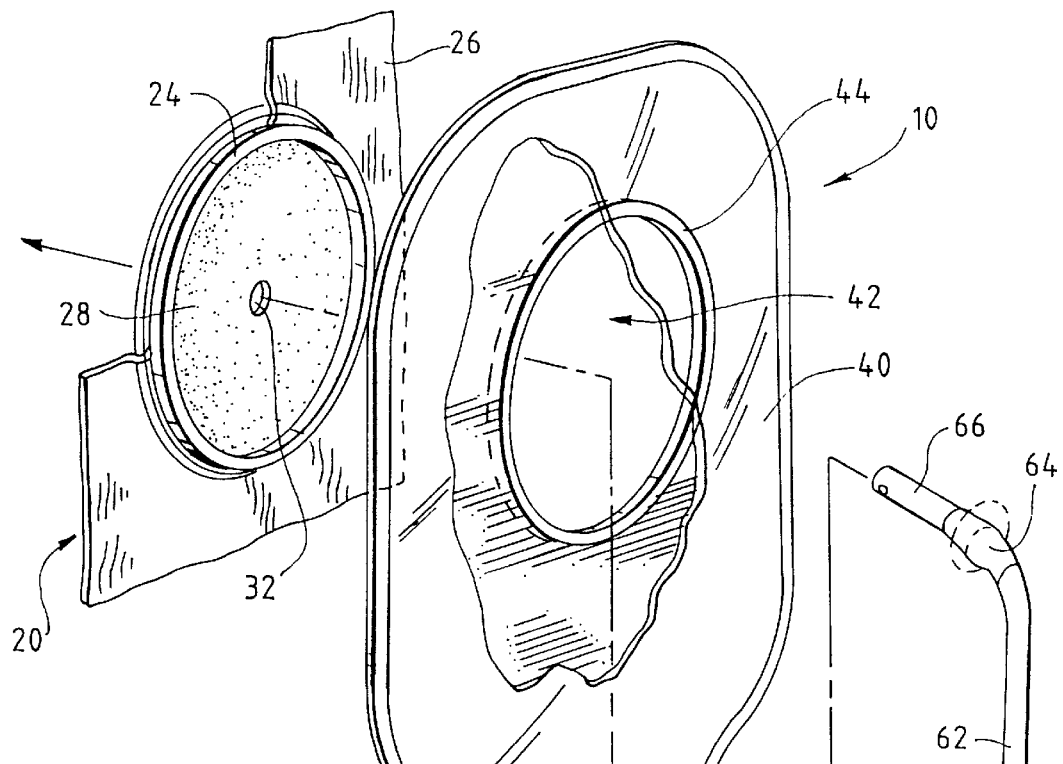
FIG. 5 is an exploded perspective view of the suprapubic leak collection device illustrated in FIG. 1.

FIG. 5 shows, in exploded form, the various components of leak collection device 10. Adhesive patch 20 consists of ring member 24 surrounding a polymeric film portion 28 with a central opening 32 formed therein. The cooperating channel member 44 of collection bag 40 circumscribes first opening 42, which communicates with opening 32 in adhesive patch 20. Catheter spout 48 is positioned within and extends from second opening 46. Opening the shut-off clamp 78 removes fluid collected in bag 40 through drainage spout 76.

As shown in FIG. 5, the first balloon 64 of urinary catheter 60 maintains the distal end 66 of catheter 60 within the patient's bladder (not shown). The second balloon 68 secures catheter tube 62 in place within catheter spout 48. First and second balloon ports 72, 74, as well as drainage port 70, are located at the proximal end 80 of catheter 60.

The following procedure is recommended for deploying the leak collection device:

1. Gather all equipment. Prep patient as in suprapubic catheter insertion procedure. A tincture of benzoine may be applied to strengthen the adherence of the adhesive patch onto the patient's skin.
2. Using sterile technique, apply the adhesive patch onto the patient, centering the patch over the patient's suprapubic ostomy site.
3. Insert the urinary catheter; introduce the appropriate amount of sterile water into the first balloon port to inflate the first balloon.
4. Position the proximal end of the catheter within the drainage spout of the collection bag. Inflate the second balloon port with air to secure the proximal end of the catheter within the drainage spout. Check for possible fluid leak. If leakage is present, add more air to the second balloon port until the leak is contained.
5. Secure the channel member of the collection bag to the ring member of the adhesive patch.
6. Connect the urinary catheter drainage port to the drainage tubing.
7. Check for return flow.

While particular elements, embodiments and applications of the present invention have been shown and described, it will be understood, of course, that the invention is not limited thereto since modifications may be made by those skilled in the art, particularly in light of the foregoing teachings. It is therefore contemplated by the appended claims to cover such modifications as incorporate those features that come within the spirit and scope of the invention.

What is claimed is:

1. A suprapubic fluid collection device for containing leakage from an ostomy site, said device comprising:
   (a) an adhesive patch having adhesive on one side thereof for securing said patch around said ostomy site, said adhesive patch having a first fastening member projecting from the other side thereof;
   (b) a collection bag having a first opening formed therein, said first opening communicating with the interior thereof, said collection bag further comprising a second fastening member projecting from the exterior of said collection bag, said second fastening member cooperating with and securing said first fastening member, said collection bag having a second opening formed therein and a drainage spout, said second opening communicating with the interior of said collection bag;
   (c) a urinary catheter extending within the interior of said collection bag between said second opening and said first opening, said catheter having a distal end for insertion within a human bladder and a proximal end, said catheter having a first inflatable balloon for securing said distal end within said bladder, a second inflatable balloon for securing and fluidly sealing said catheter within said second opening, and a drainage lumen for conducting fluid from said distal end to said proximal end for subsequent removal from the catheter.

2. The suprapubic leak collection device of claim 1 wherein said first fastening member is a ring member circumscribing the ostomy site and said second fastening member is a channel member, said channel member circumscribing said first opening and mating with and securing said ring member within said channel member.

3. The suprapubic leak collection device of claim 2 wherein said ring member has a polymeric film disposed within said ring member.

4. The suprapubic leak collection device of claim 1 wherein a tube extends from said second opening.

5. The suprapubic leak collection device of claim 4 wherein said second balloon secures and fluidly seals said tube.

6. The suprapubic leak collection device of claim 1 wherein said catheter has a first inflation lumen formed therein, said first inflation lumen capable of containing a first pressurized fluid for inflating said first balloon.

7. The suprapubic leak collection device of claim 6 wherein said first pressurized fluid is sterilized water.

8. The suprapubic leak collection device of claim 1 wherein said catheter has a second inflation lumen formed therein, said second inflation lumen capable of containing a second pressurized fluid for inflating said second balloon.

9. The suprapubic leak collection device of claim 8 wherein said second pressurized fluid is air.

10. The suprapubic leak collection device of claim 1 wherein said drainage spout has a shut-off clamp associated therewith.

* * * * *